United States Patent [19]

Knifton et al.

[11] Patent Number: 5,159,123

[45] Date of Patent: Oct. 27, 1992

[54] SYNTHESIS OF HYDROXYL-TERMINATED POLYBUTADIENES USING GLYCOL ETHER ACETATE SOLVENTS

[75] Inventors: John F. Knifton; Edward T. Marquis, both of Austin, Tex.

[73] Assignee: Texaco Chemical Company, White Plains, N.Y.

[21] Appl. No.: 694,590

[22] Filed: May 2, 1991

[51] Int. Cl.$^5$ .................. C07C 29/03; C07C 31/18
[52] U.S. Cl. .................................. 568/860; 568/852
[58] Field of Search ..................... 568/860, 857, 852

[56] References Cited
U.S. PATENT DOCUMENTS 3,459,814 8/1969 Kovach et al. ............... 568/857

Primary Examiner—Marianne M. Cintins
Assistant Examiner—Rebecca Cook
Attorney, Agent, or Firm—Jack H. Park; Kenneth R. Priem; Cynthia L. Kendrick

[57] ABSTRACT

Disclosed is an improvement in a process for polymerizing 1,3-butadiene selectively to form relatively low molecular weight hydroxyl-terminated polybutadiene oligomers in the presence of an aqueous solution of hydrogen peroxide which comprises the use of a solvent selected from the group consisting of alkylene glycol monoalkyl ether acetates and aliphatic glycol ether carboxylates to produce butadiene oligomers having a high degree of OH functionality and suppression of formation of solid or gel-type insoluble rubber by-products.

15 Claims, No Drawings

SYNTHESIS OF HYDROXYL-TERMINATED POLYBUTADIENES USING GLYCOL ETHER ACETATE SOLVENTS

FIELD OF THE INVENTION

This invention relates to the synthesis of hydroxyl-terminated polybutadienes.

More particularly this invention is directed to an improvement in a process for polymerizing 1,3-butadiene selectively to form relatively low molecular weight hydroxyl-terminated polybutadiene oligomers in the presence of an aqueous solution of hydrogen peroxide, said improvement comprising achieving butadiene oligomers having a high degree of OH functionality and suppressing the solid or gel-type insoluble rubber by-products by using a solvent selected from the group consisting of aliphatic glycol ether acetates or aliphatic glycol ether carboxylates.

BACKGROUND OF THE INVENTION

Low-molecular weight homo- and copolymers of 1,3-dienes have been known for a long time. It is advantageous for many uses to alter the properties of the hydrophobic polymers in a controlled fashion by introduction of polar groups. One of these groups is the hydroxyl group because reactions with isocyanates, for example, can be carried out on such a group.

It is also known in the art that hydroxyl-terminated polybutadiene can provide polyurethanes having good hydrolytic stability, chemical resistance and a wide range of mechanical properties.

Processes for the preparation of polyhydroxybutadiene (hydroxyl-containing butadiene homopolymers) are known in the art, and may be prepared, for example, by the methods described in U.S. Pat. Nos. 2,877,212, 3,055,952; 3,333,015; 3,338,861; 3,427,366; 3,673,168 and 3,796,762, incorporated herein by reference. For a review of polymeric butadienes see J. N. Henderson, Encyl. Polym. Sci. Eng. 515–36, 2 (1985) and W. Heitz, Telechelic Polymers: Synthesis and Applications, Chapter 4, p. 61 (1989).

In U.S. Pat. No. 4,460,801 there is disclosed a process for reacting butadiene and water in the presence of a palladium salt and boric acid in a polar, aprotic solvent to prepare an unsaturated fatty alcohol of the formula:

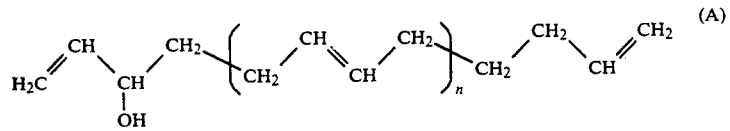

where n=2 or 4.

U.S. Pat. No. 4,670,518 discloses a process for the production of low-molecular weight homo- and/or copolymers of 1,3-dienes carrying hydroxymethyl groups partially esterified with formic acid, comprising reacting 1,3-dienes having an average molecular weight of 500–8000 with formaldehyde at temperatures of 150°–300° C. optionally in the presence of a solvent and stabilizer.

Butadiene has been polymerized with four-valence molybdenum catalysts. See M. Zhao et al., C. A. Selects, p. 12, 19 (1986). In other work $\alpha,\omega$-hydroxyl-terminated polybutadienes with different molecular weights and microstructures were prepared in nonpolar media using lithium-naphthalene-THF as a catalyst (See U.S. Pat. No. 3,055,952 and Germ. Pat. No. 1,173,658).

In U.S. Pat. No. 4,721,754 there is described a polybutadiene composition useful for the preparation of polyurea and/or polyurethane elastomers comprising a blend of a polyhydroxybutadiene homopolymer and an amine terminated polybutadiene.

A problem has existed in polybutadiene solvent recovery units wherein due to solids formation below the feed trays of the distillation columns, fouling may occur which plugs the trays and downcomers. The fouling is apparently caused by the presence of hydrogen peroxide, low molecular weight polybutadienes, polymeric precursors such as butadiene and vinylcyclohexene formed by the polymerization reaction. Such fouling may occur approximately every 5 to 6 days at high plant production rates thus requiring frequent and expensive shutdowns for cleaning.

U.S. Pat. No. 4,518,770 discloses a method of reducing the fouling in a distillation unit which comprises injecting into the distillation unit, along with the feed stream from which the polyhydroxybutadiene has been removed, an aqueous solution of an alkali metal sulfite or bisulfite.

In a Japanese patent 1012-707-A to Idemitsu Petrochem there is disclosed a method for preparing a liquid diene polymer containing OH groups prepared by reacting the conjugated diene monomer with $H_2O_2$ in the presence of carboxylic acid.

It would be extremely desirable in the art if a process were available whereby low molecular weight oligomers could be prepared which possessed a high degree of OH functionality by a method which avoided the formation of solid or gel-type insoluble rubbers that are known to foul the reactor.

SUMMARY OF THE INVENTION

In accordance with certain of its aspects, the novel method of this invention for polymerizing 1,3-butadiene to selectively form relatively low molecular weight hydroxyl-terminated polybutadiene oligomers using a process which minimizes fouling comprises polymerizing the 1,3-butadiene in the presence of an aqueous solution of hydrogen peroxide and a solvent from the group consisting of aliphatic glycol ether acetates and aliphatic glycol ether carboxylates.

This invention demonstrates an improvement over the prior art in that the hydroxyl-terminated butadiene oligomers possess low molecular weight and, at the same time, a high degree of OH functionality. Even more important is the improvement demonstrated by the process of the invention that allows for the formation of the desired oligomers without the accompanying formation of the solid or gel-type insoluble rubbers that may foul the reaction system.

DESCRIPTION OF THE INVENTION

In accordance with this invention there is provided an improved process for the preparation of oligomers of 1,3-butadiene which demonstrates a number of distinct advantages over other processes known in the related art.

The process has the following advantages: 1) The solvent can be easily removed from the system; 2) It does not interfere with the polymerization process; 3) It has miscibility with a diluted aqueous solution of hydrogen peroxide over a wide range of weight ratios; 4) It provides a product with desirable properties; and 5) It minimizes polymer build-up in the reactor system in the form of gel or solid rubber-like oligomers.

The products can be represented by the following structure:

where x, y and z are integers.

The hydroxyl-terminated polybutadiene oligomers prepared according to this invention contain hydroxyl groups that are in predominantly primary, terminal positions on the main hydrocarbon chain and are allylic in configuration. Ordinarily, at least about 1.8 hydroxyl groups are present per molecule on the average, and advantageously there are at least 2.1 to say 3 or more hydroxyls per polymer molecule, preferably 2.1 to 2.8. The diene polymer has the majority of its unsaturation in the main hydrocarbon chain, such that x plus z in the general structure (A) is greater than y. This formula (A) should not be understood as implying that the polymers are necessarily in blocks, but the cis-1,4-, trans-1,4 and vinyl(1, 2) unsaturation are usually distributed throughout the polymer molecule. The letter x may represent a number sufficient to give a trans-1,4-unsaturation content of 40–70 percent; y may be a number sufficient to give a 1,2-vinylic unsaturation content to the polymer in the range of about 10–35 percent, while z may be sufficient to provide a cis-1,4-unsaturation of about 10–30 percent. Often the polymer will contain largely trans-1,4-units, e.g. about 50–65 percent and about 15–25 percent cis-1,4-units, with about 15–25 percent 1,2-units. Branching may also occur in the above polymers, especially those prepared at higher temperatures; ether and carbonyl linkages may appear in the lower molecular weight oligomer fractions.

The number average molecular weight of the product oligomers (of general structure A) is ordinarily in the range of about 100 to about 20,000, and the hydroxyl content of said products is in the range of 0.1 to 20 meq/g, or higher. Preferably, the number average molecular weight is in the range 200 to 2000 and the hydroxyl content is in the range of 1 to 10 meq/g. Product oligomers of this type are illustrated by the accompanying examples.

Preparation of the product of this invention may be carried out typically by combining a 30 to 70% aqueous solution of hydrogen peroxide with a glycol ether acetate or carboxylate solvent and then reacting the liquid mix with 1,3-butadiene at a pressure of 0–5000 psig and a temperature of 50°–200° C. to form a one or two layered product and subsequently stripping said product or products to remove lights, solvents, etc.

The dienes which are employed to prepare the polyhydroxybutadienes include the unsubstituted, 2-substituted or 2,3-disubstituted 1,3-dienes of 4 up to about 12 carbon atoms. The diene preferably has up to 6 carbon atoms and the substituents in the 2- and/or 3-position may be hydrogen, alkyl, (generally lower alkyl, e.g., of 1 to 4 carbon atoms), aryl (substituted or unsubstituted), halogen, nitro, nitrile, etc. Typical dienes which may be employed are 1,3-butadiene, isoprene, chloroprene, 2-cyano-1,3-butadiene, 2,3-dimethyl-1,3-butadiene, 2-phenyl-1,3-butadiene, 2-methyl-3-phenyl-1,3-butadiene, etc. The examples demonstrate the particular effectiveness of 1,3-butadiene.

The aqueous solution of hydrogen peroxide is diluted with water. The $H_2O_2$ content can be in the range of 10% to 80%. Preferably the aqueous solution is in the range of about 30% to 50% $H_2O_2$. Lower contents can be used if necessary.

The molar ratio of hydrogen peroxide feed to 1,3-butadiene may vary in the range of 1:100 to 100:1, or higher, but in order to prepare desired, highly functionalized, OH-oligomers of low molecular weight, the initial $H_2O_2$:1,3-butadiene should preferably be in the range of 1:10 to 10:1 for an economically attractive process; most preferred are molar ratios of ca. 1:1.

The solvent is the critical factor in the improvement of this invention. The solvent should be able to solubilize the 50% aqueous hydrogen peroxide, the butadiene and the hydroxyl-terminated polymer into a single phase over a wide range of reactant/product ratios. In addition the solvent should be able to adequately solubilize the 1,3-butadiene at the temperature of oligomerization (ca. 50°–200° C.) in order to ensure no polymer build up in the $C_4$ entrance lines and other cooler portions of the reactor system. It is desirable that the solvent not interfere with the polymerization process nor be incorporated into the polymer product. Such a solvent system should have great commercial potential, especially if the solvent were low cost and had a low enough boiling point such that it could be easily stripped from the desired OH-oligomer product.

It has been surprisingly discovered in the process of the instant invention that certain glycol ether carboxylate solvents, including glycol ether acetates particularly alkylene glycol monoalkyl ether acetates and aliphatic glycol ether carboxylates provide all these advantages in the polymerization process. The glycol ether acetates can be aromatic or aliphatic glycol ether acetates. Aliphatic glycol monoalkyl ether acetates which work in this process include ethylene glycol monoalkyl ether acetates and carboxylates having the general structure:

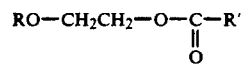

where R and R' are alkyl radicals containing one to ten, preferably 1 to 6, carbon atoms that may, or may not, be different, but which are typically methyl, ethyl, isopropyl, t-butyl and n-hexyl. Typical examples include ethylene glycol monomethyl ether acetate, ethylene glycol monoethyl ether acetate, ethylene glycol monomethyl ether propionate, ethylene glycol monobutyl ether acetate, ethylene glycol mono-t-butyl ether acetate, ethylene glycol monopropyl ether acetate and ethylene glycol monohexyl ether acetate.

Suitable propylene glycol monoalkyl ether carboxylates would have the general structure:

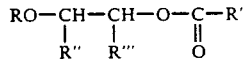

where R and R' are alkyl radicals containing one to ten, preferably 1 to six, carbon atoms that may, or may not, be different, as described above, and R" and R'" are either hydrogen, or the methyl radical. Typical examples include propylene glycol monomethyl ether acetates, propylene glycol monobutyl ether acetates or propylene glycol mono-t-butyl ether acetates. Said propylene glycol monoalkyl ether carboxylates may, or may not, be a mixture of isomeric forms.

Suitable aromatic glycol ether acetates include 2-phenoxylethyl acetate and p-methoxyphenoxyethyl acetate.

Generally, the aliphatic glycol ether carboxylates suitable for the practice of this invention are made from aliphatic carboxylic acids with 1 to 6 carbon atoms. Examples include acetic acid, propionic acid and the butyric acids.

The examples herein demonstrate that good results have been achieved with ethylene glycol monomethyl ether acetate and propylene glycol monomethyl ether acetate.

While the hydroxyl components of the product polyhydroxybutadienes are predominantly primary, terminal and allylic in structure, both the ratio of cis-1,4, trans-1,4 and 1,2-vinyl unsaturation which occurs in the diene polymers prepared by this invention, in addition to the number and location of the hydroxyl groups, and the molecular weight of the polymers, can be a function of polymerization conditions, particularly the temperature, the $H_2O_2$ to 1,3-butadiene feed ratio, and the type of addition polymerization system employed in forming the polymer. It has been found that diene polymers of the desired configuration can be obtained using hydrogen peroxide as the initiator for polymerization in a suitable solvent system. This free-radical addition polymerization usually takes place in solution at a temperature above about 50° C. to 200° C.

The polymerization may be conducted batchwise in a continuous slurry reactor, or in a stirred tank, continuous flow reactor.

Polymerization of 1,3-butadiene in the presence of about 50% $H_2O_2$ can generally be conducted at temperatures from 100° C. to 150° C. The operating pressure may be from zero to 5000 psig. The most preferred temperature range is about 110°–130° C. and the preferred pressure range is about 100 psig to 1000 psig.

Example 1 illustrates the syntheses of desired low molecular weight hydroxyl-terminated polybutadiene oligomers having a high degree of hydroxyl functionality using hydrogen peroxide as initiator and ethylene glycol monoethyl ether acetate as solvent.

Advantages to using said solvent include:
a) Its miscibility with 50% aqueous hydrogen peroxide over a wide range of weight ratios.
b) It does not interfere with the polymerization process or the formation of desired hydroxyl-terminated polybutadiene oligomer.
c) It can be easily removed from the desired oligomer product.

Example 2 illustrates the synthesis of desired low molecular weight hydroxyl-terminated polybutadiene oligomers of the same type using propylene glycol monomethyl ether acetate as the solvent of choice.

EXAMPLE 1

To a 300 cc capacity, stirred clave reactor fitted with temperature and pressure controls plus facilities for two continuous feed additions, was charged with ethylene glycol monomethyl ether acetate, and the reactor heated to temperature (120° C.) under pressure (600 psi). A liquid mix of 50% hydrogen peroxide aqueous solution (2 parts) and ethylene glycol monomethyl ether acetate (3 parts) was then fed continuously to said reactor at a rate of 300g/hr (1.76 moles $H_2O_2$/hr), and when the system was lined out, a second feed of 1,3-butadiene was also introduced simultaneously at a rate of 100 g/hr (1.85 moles/hr). After a few hours on stream, typical liquid product was collected under these steady state conditions for about 30 hours.

The two-phase liquid product was allowed to stand and the two layers separated. A sample (1462 g) of the top layer was stripped to remove lights, solvent, etc., and the residue, water-white liquid (1026 g) analyzed as follows:

| | |
|---|---|
| Number Average mw | 11.83 |
| Weight Average mw | 2154 |
| Dispersity | 1.8 |
| Viscosity | 2900 cs/25° C. |
| Hydroxyl Number | 1.6 meq KOH/g |

$^{13}C$ NMR analyses of this product shows the total carbon association with the three major functionalities of this material, olefin, OH and aliphatic, to be about 47, 6.6 and 46%, respectively. A sample (4505 g) of the heavier layer was likewise stripped to remove lights, solvent, etc., and the residual liquid (633 g) analyzed as follows:

| | |
|---|---|
| Number Average mw | 246 |
| Weight Average mw | 543 |
| Dispersity | 2.2 |
| Viscosity | 2998 cs/25° C. |
| Hydroxyl Number | 8.7 meq KOH/g |

EXAMPLE 2

Using the same 300 cc capacity, stirred autoclave reactor system of Example 1, as well as the same start-up procedures, said reactor was charged with a mix of 50% hydrogen peroxide solution (2 parts) and 1,2-propylene glycol monomethyl ether acetate (3 parts) at a rate of 300 g/hr (1.76 moles $H_2O_2$/hr), plus 1,3-butadiene at 100 g/hr (1.85 moles/hr). Operating conditions were 120° C. and 600 psi. Liquid product was collected from the unit for about 24 hours under steady state conditions.

The two-phase liquid product was allowed to stand at ambient temperature and the two layers separated. A sample of the top layer (1043 g) was stripped to remove lights, solvent, etc., and the residual liquid (637 g) analyzed as follows:

| | |
|---|---|
| Number Average mw | 1534 |
| Weight Average mw | 2689 |
| Dispersity | 1.8 |
| Viscosity | 5352 cs/25° C. |
| Hydroxyl Number | 2.2 meq KOH/g |

A sample of the heavier layer (6865 g) was likewise stripped to remove lights, solvent, etc., and the residual liquid (708 g) analyzed as follows:

| | |
|---|---|
| Number Average mw | 251 |
| Weight Average mw | 643 |
| Dispersity | 2.6 |
| Hydroxyl Number | 10.5 meq KOH/g |

What is claimed is:

1. In a process for the preparation of hydroxyl-terminated polybutadiene oligomers having an average molecular weight of 100 to 20,000 and a hydroxyl content of 0.1 to 20 meq/g by reacting 1,3-butadiene with an aqueous solution of hydrogen peroxide, the improvement consisting essentially of the use of a solvent selected from aliphatic glycol ether carboxylates derived from aliphatic carboxylic acids with 1 to 6 carbon atoms.

2. The process of claim 1 wherein the hydroxyl-terminated polybutadiene oligomers have a number average molecular weight of 200 to 2000, and a hydroxyl content of 1 to 10 meq/g.

3. The process of claim 1 wherein the aqueous hydrogen peroxide solution is about 10 to 80%.

4. The process of claim 1 wherein the aqueous hydrogen peroxide solution is about 50%.

5. The process of claim 1 wherein the hydrogen peroxide feed to 1,3-butadiene molar ratio is in the range of 100:1 to 1:100.

6. The process of claim 1 wherein the hydrogen peroxide to 1,3-butadiene molar ratio is in the range from 10:1 to 1:10.

7. The process of claim 1 wherein the aliphatic glycol ether carboxylate solvent is an alkylene glycol monoalkyl ether acetate selected from the group consisting of ethylene and propylene glycol monoalkyl ether acetates.

8. The process of claim 1 wherein the glycol ether carboxylate solvent is an alkylene glycol monoalkyl ether acetate solvent selected from the group consisting of ethylene glycol monomethyl ether acetate and propylene glycol monomethyl ether acetate.

9. The process of claim 1 wherein the glycol ether carboxylate solvent is ethylene glycol monomethyl ether acetate.

10. The process of claim 1 wherein the glycol ether carboxylate solvent is propylene glycol monomethyl ether acetate.

11. The process of claim 1 wherein the aliphatic glycol ether carboxylate is made from a carboxylic acid selected from acetic acid or propionic acid.

12. The process of claim 1 wherein the product is a two-layered liquid.

13. The process of claim 1 wherein the temperature is from about 50° C. to 200° C.

14. The process of claim 1 wherein the pressure is from 0 to about 5000 psig.

15. The process of claim 1 wherein the hydrogen peroxide to 1,3-butadiene molar ratio is about 1:1 and said process is conducted in a continuous, stirred-tank, reactor design.

* * * * *